United States Patent [19]

Krbechek et al.

[11] Patent Number: 5,300,689
[45] Date of Patent: Apr. 5, 1994

[54] OXIMATION PROCESS

[75] Inventors: Leroy O. Krbechek, Santa Rosa, Calif.; Mary I. Casey, Bishopstown, Ireland

[73] Assignee: Henkel Corporation, Ambler, Pa.

[21] Appl. No.: 854,522

[22] Filed: Mar. 20, 1992

[51] Int. Cl.$^5$ .......................................... C07C 249/08
[52] U.S. Cl. .................................................... 564/259
[58] Field of Search .......................................... 564/259

[56] References Cited

U.S. PATENT DOCUMENTS

| | | | |
|---|---|---|---|
| 3,449,066 | 6/1969 | Swanson | 423/59 |
| 3,592,775 | 7/1971 | Swanson | 564/266 |
| 4,128,580 | 12/1978 | Matsumoto et al. | 564/259 |
| 4,133,834 | 1/1979 | Pickens | 260/566 A |
| 4,507,268 | 3/1985 | Kordosky et al. | 423/24 |
| 4,868,334 | 9/1989 | Mathew et al. | 564/264 |

FOREIGN PATENT DOCUMENTS 9118867 12/1991 PCT Int'l Appl. .

OTHER PUBLICATIONS

Mathur et al. "Laboratory Experiments on Phase Transfer-Catalyzed Reactions of Neutral Molecules" *J. Chem. Ed.*, 67, p. 273, Mar. 1990.

*Primary Examiner*—Richard L. Raymond
*Assistant Examiner*—P. O'Sullivan
*Attorney, Agent, or Firm*—Ernest G. Szoke; Wayne C. Jaeschke; Patrick J. Span

[57] ABSTRACT

An improved process for oximation of carbonyl compounds, such as ketones and aldehydes by oximation with hydroxylamine including oximation processes carried out in the presence of a catalytic amount of an acid phase transfer catalyst, such as 2-ethylhexanoic acid, and/or the presence of an alkali metal or alkaline earth metal catalyst. The resulting oximes are useful as metal extractants.

34 Claims, No Drawings

OXIMATION PROCESS

BACKGROUND OF THE INVENTION

1. Field of the Invention

This invention relates to the preparation of oximes from essentially water insoluble carbonyl compounds, i.e. ketones or aldehydes, and in particular to improved processes which may employ a phase transfer catalyst. Hydroxyoximes prepared by the improved method are useful as metal extractants.

2. Description of Related Art

As described in U.S. Pat. No. 4,868,334, oximes are generally produced by reacting an organic carbonyl compound such as an aldehyde or ketone with hydroxylamine, usually generated from a hydroxylamine salt such as hydroxylammonium sulfate or hydroxylammonium chloride.

Current oximation procedures, particularly of long alkyl chain ketones, employ standard oximation processes with an alcohol, such as methanol as a solvent, hydroxylammonium sulfate and sodium acetate. Since sodium acetate must be anhydrous and is considerably more expensive than sodium carbonate, attempts have been made to employ sodium carbonate in the ketoximation procedure, but such attempts have not been successful.

U.S. Pat. No. 4,133,834 describes the general preparation of alpha and beta-hydroxyoximes generally useful as extractants for metals such as copper from aqueous solutions and discusses, as exemplary processes, those of U.S. Pat. No. 3,449,066 and 3,592,775 relative to the preparation of aliphatic, alpha-hydroxyoximes, from the corresponding acyloins and beta-hydroxyoximes from the corresponding aromatic phenones. In each of the processes the reaction is carried out under reflux conditions with an hydroxylamine salt in an alcohol medium (such as methanol) in the presence of a weak base, such as sodium acetate. Such methods typically required long reaction times for completion, particularly when the oximes included aromatic groups. The U.S. Pat. No. 4,133,834 describes a process for reducing the time of reaction by employing catalytic amounts of iron, $Fe^{+2}$ and $Fe^{+3}$. Nawal K. Mathur and Chander K. Narang, in "Laboratory Experiments on Phase-Transfer-Catalyzed Reactions of Neutral Molecules", *J. Chem. Ed.*, 67, p. 273, March 1990, describe the oximation of benzophenone by first preparing an aqueous solution of hydroxylammonium chloride (1 equiv/equiv of ketone) in water and neutralizing with sodium hydroxide 1 equiv). This results in high concentration of free hydroxylamine being present all at once, which in large scale operations would present an unsafe condition. To this is added an equal volume of toluene containing 1 equivalent of benzophenone and 1 equivalent (stoichiometric amount) of 2-ethylhexanoic acid at 60° C for 1.5 hour. In the reaction mixture the level of water is 53.5 moles/mole of carbonyl and the level of toluene was 4.76 g/g of ketone. The 2-ethylhexanoic acid allegedly acts as a bifunctional catalyst, i.e. a weak acid catalyst as well as a phase transfer catalyst.

The oximes, such as the hydroxy aryl ketoximes and hydroxy aryl aldoximes, which are substantially insoluble in water but soluble in water immiscible, organic solvents, such as kerosene, are useful in solvent extraction processes for recovery of metals, particularly copper, from aqueous solutions. U.S. Pat. No. 4,507,268, describes a number of such oxime reagents prepared from ketones and aldehydes, and the use thereof in liquid/liquid extraction processes.

DESCRIPTION OF THE INVENTION

In this description, except in the operating examples or where explicitly otherwise indicated, all numbers describing amounts of ingredients or reaction conditions are to be understood as modified by the word "about" in describing the broadest scope of the invention. Practice of the invention within the exact numerical limits is however generally preferred.

It has now been discovered that carboxylic acids having from about 4 to about 20, preferably about 6 to about 18 carbon atoms, when employed in the oximation process catalyze the oximation of carbonyl containing compounds, acting as a phase transfer catalyst, to accelerate the rate at which the carbonyl compounds, ketones or aldehydes, are oximated. Particularly in regard to the oximation of the ketones, the use of these phase transfer catalysts, provide additional unexpected advantages. Firstly, alcohol solvents may be avoided thereby reducing any flammability hazards, as well as eliminating environmental concerns which normally require recovery by stripping of the methanol together with the attendant cost of stripping equipment. Secondly, sodium carbonate may be employed in the process of oximation of the ketones, eliminating the necessity for anhydrous sodium acetate, which is not only expensive, but which also results in the generation of acetic acid in the reaction requiring further treatment and equipment for handling of the acetic acid. Thus, the environmental benefits of the present invention are many.

One aspect of the present invention accordingly provides for an improved process of oximation of carbonyl compounds (ketones or aldehydes), comprising
  (a) reacting a carbonyl compound with hydroxylamine in the presence of
    (1) a catalytic amount of a phase transfer acid catalyst and
    (2) an alkali metal or alkaline earth metal hydroxide and carbonate (including bicarbonate) to form the oxime of said carbonyl compound; and
  (b) recovering the resulting oxime from the reaction mixture.

The present invention is directed to the oximation of carbonyl compounds, and in particular to oximation of ketones or aldehydes, the oximes of which are useful in the extraction of metal values, such as copper, from aqueous leach solutions. While the process of the present invention may be applied generally to the preparation of oximes of ketones or aldehydes generally, it is of particular value to the preparation of aliphatic or aromatic oximes useful for extraction of metal values from aqueous solutions, which oximes are substantially insoluble in water but are soluble in water immiscible organic solvents such as kerosene, such as those described in U.S. Pat. No. 4,507,268 noted earlier above.

The present invention is accordingly useful in the preparation of hydroxy aryl ketoximes and aldoximes of the type described in U.S. Pat. No. 4,507,268 from the corresponding ketones or aldehydes. As described in the patent such hydroxy aryl ketoximes and aldoximes are ideally defined by the formulas I, II and III:

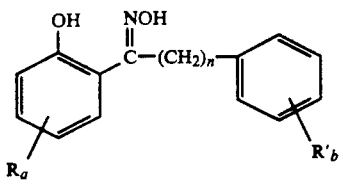

(I)

in which R and R' may be individually alike or different and are saturated aliphatic groups of 1–25 carbon atoms, ethylenically unsaturated aliphatic groups of 3–25 carbon atoms or —OR" where R" is a saturated or ethylenically unsaturated aliphatic group as defined; n is 0 or 1; and a and b are each 0, 1, 2, 3 or 4, with the proviso that both are not 0 and the total number of carbon atoms in $R_a$ and $R'_b$ is from 3 to 25;

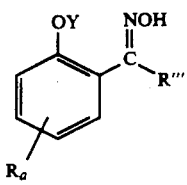

(II)

in which R and a are as defined with respect to Formula I and R''' is a saturated aliphatic group of 1–25 carbon atoms or an ethylenically unsaturated aliphatic group of 3–25 carbon atoms, with the proviso that the total number of carbon atoms in $R_a$ and R''' is from 3 to 25, and Y is H or R''';

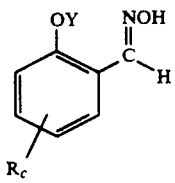

(III)

in which R and Y are as defined above with respect to Formulas I and II, c has a value of 1, 2, 3 or 4, and the total number of carbon atoms in $R_c$ is from 3 to 25. Preferred compounds of Formula III are those wherein c is 1, R is a straight or branched chain alkyl group having from 7 to 12 carbon atoms, and wherein R is attached in a position para to the hydroxyl group. Among these, the more preferred are those wherein R is a mixture of isomers. Compounds of Formula III which are especially useful in the practice of metal extraction include 2-hydroxy-5-heptyl benzaldoxime, 2-hydroxy-5-octylbenzaldoxime, 2-hydroxy-5-nonylbenzaldoxime and 2-hydroxy-5-dodecylbenzaldoxime. Compounds of Formulas I and II which are especially useful in the practice of metal extraction include: 2-hydroxy-5-nonylbenzophenone oxime; 2-hydroxy-5-dodecylbenzophenone oxime; 2-hydroxy-5-nonylphenyl benzyl ketone oxime; and 2-hydroxy-5-nonylphenyl methyl ketone oxime.

Aliphatic oximes which may be prepared by the present invention and which are useful as extractants for metal are alpha-hydroxy aliphatic oximes such as described in U.S. Pat. Nos. 3,428,449 and 3,449,066, prepared from the corresponding aliphatic ketones. Such α-hydroxyoximes have the idealized structural formula IV

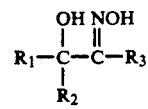

IV where $R_1$ and $R_3$ are alkyl groups of 1 to about 14 carbon atoms and $R_2$ is H or an alkyl group of 1 to about 14 carbon atoms, and the oxime being further characterized as having a total carbon atom content of 8 to 44. A preferred aliphatic oxime is 5,8-diethyl-7-hydroxydodecan-6-oxime prepared from 5,8-diethyl-7-hydroxydodecan-6-one. Other illustrative aliphatic oximes such as described in U.S. Pat. No. 3,449,066 are 7-n-butyl-7-hydroxydodecan-6-oxime, 6-ethyl-6-hydroxydodecan-5-oxime, 6-n-butyl-6-hydroxydodecan-5-oxime, 7-n-pentyl-7-hydroxy-tridecan-6-oxime, and 9-ethyl-7-n-pentyl-7-hydroxy-tridecan-6-oxime.

As indicated, the oxime is prepared by oximation of the corresponding ketone or aldehyde with hydroxylamine. The hydroxylamine is preferably employed in the form of a salt thereof, preferably the sulfate, halide (chloride or bromide) or phosphate and the like. The least expensive and most preferred is the sulfate. Raschig hydroxylamine may be employed, which is raw product from the Raschig process for the production of hydroxylamine. Raschig hydroxylamine is a solution of hydroxylammonium sulfate (11 weight %), ammonium sulfate (23 weight %) sulfuric acid (about 7.5 weight %) and water (about 58.5 weight %).

The hydroxylamine, preferably the sulfate (hydroxylammonium sulfate), is employed in an amount of at least 1 equivalent to 1 equivalent of carbonyl, and preferably in a slight excess up to about 15 to about 50 equivalent percent, i.e. up to 1.5 equivalents of hydroxylamine to carbonyl. Preferably, the hydroxylamine is employed in an excess amount of about 1.1 equivalent/equivalent carbonyl. Thus, the hydroxylamine will preferably be employed in an equivalents ratio of hydroxylamine to carbonyl greater than 1:1 up to about 1.15 or about 1.2:1 and preferably about 1.1:1.

The reaction of the ketone or aldehyde with hydroxylamine is carried out in the present invention in the presence of a catalytic amount of a phase transfer acid catalyst. The preferred acids employed as a phase transfer catalyst are the weak organic carboxylic acids, aliphatic or aromatic, containing from about 4 to about 20 carbon atoms, most preferably about 6 to about 10 carbon atoms. The preferred acid employed in the present invention is 2-ethylhexanoic acid. Other acids which may be employed are the organo phosphorous or sulfonic acids.

The phase transfer catalyst is employed in catalytic amounts up to about 0.2 moles of acid per mole of carbonyl, preferably from about 0.001 to about 0.1 moles acid/mole of carbonyl, with about 0.04 moles acid/mol of carbonyl being most preferred.

The reaction of the hydroxylamine with the carbonyl compound (ketone or aldehyde) is conducted in the presence of an alkali metal or alkaline earth metal hydroxide or carbonate (including bicarbonate). While sodium carbonate is preferred, the other alkali metal carbonates may be employed such as potassium or lithium carbonate. Calcium carbonate is preferred as an alkaline earth metal carbonate replacement for the sodium carbonate.

The alkaline compound is employed in at least a stoichiometric amount to the hydroxylamine salt, i.e. at least 1 equivalent carbonate to 1 equivalent hydroxylamine salt, although a slight excess is preferred up to about 15 to about 50% excess. Thus, the carbonate will preferably be employed in an equivalent ratio of carbonate to hydroxylamine greater than 1:1, up to about 1.5:1, and preferably about 1.1:1.

While not intended to be limited thereto, the reaction is believed to proceed as indicated below. The 2-ethylhexanoic acid serves as a phase transfer catalyst and reacts at the surface of the sodium carbonate to form the sodium salt of the acid, water and carbon dioxide. The sodium salt of the acid can then react at the surface of the hydroxylammonium sulfate to form sodium sulfate and the hydroxylammonium salt of 2-ethylhexanoic acid. The resultant hydroxylammonium salt of 2-ethylhexanoic acid is soluble in the organic phase and can react with the ketone or aldehyde to form the desired oxime, water and regenerate the 2-ethylhexanoic acid. In the absence of the phase transfer catalyst, the 2-ethylhexanoic acid, the reaction may not go to completion even after extended time periods above about 7 hours.

As can be seen from the foregoing discussion, some water should preferably be present, if only in a small amount sufficient to wet the surfaces of the hydroxylammonium sulfate and sodium carbonate crystals. As Raschig hydroxylamine contains water, no added water is required. If none of the reactants or solvent media contain any water, where the system would otherwise be an anhydrous one, a small amount of water, sufficient to wet the surfaces of the hydroxylammonium sulfate and sodium carbonate crystals, will preferably be added. Preferably, water is present in the reaction mixture, either added water or byproduct water of reaction up to an amount of about 10 moles of water per mole of carbonyl, preferably at least about 0.1 mole water/mole of carbonyl. Preferably the water will be present in an amount of about 0.5 mole to 5 moles water/mole of carbonyl, with about 1 mole water/equivalent carbonyl being most preferred.

The reaction may be conducted in the absence of solvent. It is, however, preferred to carry out the reaction employing a hydrocarbon solvent, such as toluene. The presence of the hydrocarbon solvent provides several advantages. The toluene solvent serves to thin the reaction mixture somewhat to prevent excessive foaming due to evolution of carbon dioxide as the reaction progresses. The hydrocarbon solvent accordingly insures that minimal foaming problems arise. The hydrocarbon solvent also promotes better dispersal of the reaction components thereby providing further reduction in reaction time. The presence of the solvent, such as toluene, also provides a safety feature as the temperature may be kept fairly constant at the toluene-water azeotrope reflux temperature, thereby minimizing any hazard which may be associated with the use of hydroxylamine at high temperatures. Toluene is the preferred hydrocarbon solvent, however other inert, aliphatic or aromatic hydrocarbon solvents may be employed, such as xylene, hexane, heptane, ethers and kerosene.

The reaction in the present invention will be complete, or substantially complete in from about 1 to 7 hours, dependent on the particular temperature of reaction. With aldehydes, such 5-nonylsalicylaldehyde or 5-dodecylsalicylaldehyde, the operative temperature range may extend from about 35° C. to about 95° C., with about 50° to about 90° C. being preferred. With ketones, such as 2-hydroxy-5-nonylacetophenone, the temperature will extend from about 50° to about 95° with temperatures above about 60° C. being preferred, temperatures of about 75° C. to about 90° C. being the most desirable, most preferably about 90° C. With the presence of a hydrocarbon solvent such as toluene, the reaction will be generally conducted at the reflux temperature of the toluene-water azeotrope.

The reaction is preferably conducted with agitation (stirring) to reduce the reaction time. At preferred temperatures of 75°-90° C., with agitation, the reaction will generally be complete within about 4 hours. After completion of the reaction, the oxime reaction product is generally diluted with toluene, followed by a water wash. The first water wash will be very high in salts, which may tend to precipitate on cooling. Accordingly, until diluted, this wash water should preferably be kept hot, i.e. 40°-50° C.

In the foregoing description, the oximation has been described employing both a phase transfer catalyst and an alkaline compound (hydroxide, carbonate or bicarbonate). When the carbonyl compound is an aldehyde, such as 5-nonylsalicylaldehyde (hereinafter referred to as NSA), the use of the phase transfer catalyst, such as the 2-ethylhexanoic acid provides for significant acceleration of the reaction. However in the case of the aldehydes, such as 5-nonylsalicylaldehyde, the nonylsalicylaldehyde is a stronger acid than is, for example, 2-hydroxy-5-nonylacetophenone (hereinafter HNA), and the NSA may function itself as a phase transfer catalyst, much as the 2-ethylhexanoic acid, reacting first at the sodium carbonate surface and then at the hydroxylammonium sulfate surface to extract hydroxylamine into the organic phase followed by reaction to produce the oxime. Because of somewhat weaker acidity of HNA, it may not be able to function as a phase transfer catalyst, and accordingly with such ketone, it is generally necessary to employ the 2-ethylhexanoic acid as a phase transfer catalyst to effect the desired acceleration of the rate of reaction. With the aldehyde, a significant rate of reaction may be achieved without the use of a phase transfer catalyst such as 2-ethylhexanoic acid, though use of the phase transfer catalyst will provide even further acceleration of the rate of reaction and reduced reaction times. In the absence of any phase transfer catalyst, the presence of the alkaline compounds earlier described, the alkali metal or alkaline earth metal hydroxide, carbonate or bicarbonate, are employed. The alkaline compound is employed preferably in a buffering capacity in a hydrocarbon solvent such as those earlier described, although the reaction may be conducted in the absence of hydrocarbon solvent. Again water is present in amounts as earlier described above. This aspect of the invention is particularly applicable to the preparation of 5-alkylsalicylaldoximes from the corresponding aldehydes in which the alkyl groups have from about 6 to about 11 carbon atoms, preferably about 7 to about 9 carbon atoms.

Accordingly, this invention also provides a process for the preparation of alkylsalicylaldoximes in which the alkyl group contains from about 6 to about 10 carbon atoms comprising:
(i) reacting an alkylsalicylaldehyde in which the alkyl groups contain from about 6 to about 10 carbon atoms with hydroxylamine in the presence of
(x) an alkaline compound selected from the group of an alkali metal or alkaline earth metal hydroxide, carbonate and bicarbonate, and (y) water in an amount sufficient to wet the surfaces of the hydroxylamine and the alkaline compound; and (ii) recovering the resulting oxime from the reaction mixture.

The earlier description in relation to oximation of aldehydes as to the reactants, amounts and conditions of reaction apply. The preferred salicylaldehydes are the heptyl, octyl and most preferably the nonylsalicylaldehyde. The preferred hydroxylamine source is hydroxylamine sulfate and the preferred alkaline compounds are sodium hydroxide or sodium carbonate. Where a hydrocarbon solvent is employed, toluene is preferred. The preferred temperature of reaction is from about 60° to about 90° C. The preferred amounts of the materials are the same as earlier described.

To further illustrate the various objects and advantages of the present invention, the following examples are provided in which all parts and percentages are by weight unless otherwise indicated. It is understood that their purpose is entirely illustrative and in no way intended to limit the scope of the invention.

In the examples, the following codes or abbreviations are employed:
HNA—2hydroxy-5-nonylacetophenone
NSA—5-nonylsalicylaldehyde
DSA—5 dodecylsalicylaldehyde
HAS—hydroxylammonium sulfate
EHA—2-ethylhexanoic acid
TLC—thin layer chromatography
IR—infra red
GC/FTIR—Gas chromatography/Fourier Transform Infra Red
HPLC—High pressure liquid chromatography
Versatic 10 acids—a mixture of isomeric $C_{10}$ acid available from Shell Chemical.

EXAMPLE 1

This example serves to illustrate the acceleration of the rate at which carbonyl compounds are oximated by the addition of a carboxylic acid.

A. The reaction mixture was comprised of a mixture of 96.9 grams of HNA (81% purity—0.3m); 27.06 grams of HAS (0.165 m); 20.0 grams of sodium carbonate (0.19 m) and 5.4 grams of water. The temperature was raised to 90° C. and samples withdrawn after hour, 3 hours and 5 hours. After 1 hour the product contained 30% unoximated ketone, 7.5% after 3 hours and 2% after 5 hours.

B. For comparison, illustrating the present invention 1.15 grams of EHA was added to a mixture identical to A above and the reaction repeated at 90° C. After hour the product contained 13% unoximated ketone, 3% after 3 hours and 0.5% after 5 hours.

EXAMPLE 2

A reaction mixture consisting of 783 parts toluene; 3,413 parts HNA approximately 82% purity; 700 parts sodium carbonate; 100 parts water; 950 parts HAS and 60 parts 2-EHA were combined at 60° C. and the temperature raised to 90° C. The product contained 0.9% residual ketone after 35 minutes at 90° C. and 0.5% after 3 hours.

EXAMPLE 3

In this example, the reaction mixture contained 96.7g HNA (81% ketone—0.3 m); 27.06 g HAS (0.165 m); 20.0 g sodium carbonate (0.19 m); 2.7 g Versatic 10 acids (0.016 m) and 5.4 g water. The mixture was heated at 96°–99° C. for 5 hours and 101 g of product was isolated. Under these conditions, no residual ketone was reported by IR (<0.5% detection limit) or laboratory TLC. The workup proceeded well, involving first dilution with toluene, followed by washing with water at 70° C., followed by washing with a 1% solution of sodium carbonate and twice with water. Clean phase splits occurred and no residual carboxylic acids were detected by IR.

The reaction can also be run as a two-phase aqueous/organic system. No detectable ketone was present in a reaction mixture which consisted of 32.3 g of HNA (0.1 m); 11 g of HAS (0.067 m); 14.3 g of sodium carbonate (0.135 m); 1.62 g of Versatic 10 acids (0.0095 m); 10 ml of toluene and 10 ml of water after being stirred at 60 deg for 9 hours.

EXAMPLE 4

In this example the reaction charge was:
96.9 g HNA (81%–0.3 m)
27.06 g HAS (0.165 m)
20.0 g sodium carbonate (0.19 m)
5.4 g water (0.3 m)

The reaction charge was heated in three oximations at the temperatures and the results shown below:

TABLE 1

| | % Ketone | | | | | |
|---|---|---|---|---|---|---|
| | No Catalyst | | 1.15 g EHA Catalyst | | | |
| | 90° C. | | 90° C. | | 75° C. | |
| Time | TLC | IR | TLC | IR | TLC | IR |
| 1 | 60 | 30 | <50 | 13 | | |
| 2 | <50 | 14 | 20 | 5.5 | | |
| 3 | 20 | 7.5 | 5 | 3 | | |
| 4 | 10 | 4 | 0.5–1 | 1 | 10–15 | — |
| 5 | 5 | 2 | <0.5 | 0.5 | 0.5–2 | — |
| 6 | 5 | 1 | Trace | 0 | <1 | 1 |
| 7 | 2 | 0.5 | | | <1 | — |
| 8* | Trace | — | | | Trace | 0 |

*7 hour reaction temperature, overnight at room temperature, followed by 1 hour at reaction temperature The foregoing illustrates that at 90° C., the oximation is accelerated by the addition of the 2-ethylhexanoic acid phase transfer catalyst, the reaction being substantially complete in about 4 hours with 0 or a trace of ketone by 6 hours, in comparison with the use of no catalyst which showed a trace of ketone only after about 8 hours. Reaction at 75° C. with the EHA catalyst took about 5–6 hours for substantially complete reaction showing less than 1% ketone at 6 hours.

EXAMPLE 5

In this example, a laboratory oximation at 75° C. was conducted with stirrer agitation at 500 rpm. The reaction charge was 1 kg HNA, 279 g HAS, 206 g sodium carbonate, 56 g water and 35.6 g EHA added to the charge at 75° C. over a 15 minute time period, which caused an exotherm to 80° C. to occur. The temperature was maintained at 75° C. for 4 hours. After 3 hours, the product had a ketone content measured by IR of 2.5% and only a trace at 4 hours.

EXAMPLE 6

In this example, large scale batch ketoximations were carried out to determine the practicality of operation of the EHA-sodium carbonate oximation of HNA on a full-size plant scale.

The materials were charged to the reactor in the order and amounts indicated in the following Table 2.

TABLE 2

| Material | Weight-Kg |
|---|---|
| Toluene | 786 |
| HNA | 3413 |
| Sodium Carbonate | 700 |
| Water | 100 |
| HAS | 950 |
| EHA | 60 to 120 |

The reactor contents were then carefully heated to 90° C., taking care to avoid the pot temperature exceeding 95° C. to avoid any decomposition of the HAS. Samples were taken to determine residual ketone. After completion of the reaction, the product is washed employing the following in the order indicated in the following Table 3.

TABLE 3

| Washing Material | Weight Kg |
|---|---|
| Toluene | 1122 |
| Water (3 washes of) | 3000 |
| Kerosene | 898 |

The conditions and results of the large size batch oximations can be seen from the following Table 4.

TABLE 4

| Batch No. | Hrs. Reflux | Residual HNA | Yield Kg HNA Oxime | Init Pot Temp °C. | Reaction Temp °C. | Water Wash Temp °C. | EHA Kgs |
|---|---|---|---|---|---|---|---|
| 1 (¼ batch) | 4 | 0.44 | 2150 | 33 | 90 | 60 | 60 |
| 2 (¼ batch) | 3 | 0.2 | 2095 | 33 | 90 | 60 | 60 |
| 3 | 2/3 | 1.6/1.0 | 4235 | 33 | 90 | 60 | 120 |
| 4 | 3 | 0.3 | 3790 | 33 | 90 | 50 | 90 |
| 5 | 3 | 0.5 | 4560 | 40 | 90 | 50 | 90 |
| 6 | 3 | 0.6 | 4320 | 50 | 90 | 50 | 90 |
| 7 | 3 | 0.5 | 4200 | 50 | 90 | 50 | 90 |
| 8 | 3/5 | 0.9 | 4225 | 50 | 90 | 70 | 60 |
| 9 | 5 | 1.3/0.3 | 4160 | 60 | 90 | 70 | 60 |
| 10 | 3 | 0.7 | 4220 | 60 | 90 | 70 | 60 |
| 11 | 3 | 0.8 | 4290 | 60 | 90 | 70 | 60 |
| 12 | 3/4 | 1.1/0.5 | 4175 | 60 | 90 | 70 | 60 |
| 13 | 3/4 | 1.2/0.7 | 4190 | 60 | 90 | 70 | 60 |
| 14 | 3/4 | 1.4/0.8 | 4240 | 60/30 | 90 | 70 | 60 |
| 15 | 3 | 1.0 | 4130 | 60 | 90 | 70 | 60 |
| 16 | 4.5 | 0.9 | 4190 | 50 | 90 | 70 | 60 |
| 17 | 5 | 0.9 | 4130 | 50 | 90 | 70 | 60 |

The resulting oxime of batch 4 of the 2-hydroxy-5-nonylacetophenone prepared above was evaluated and compared to a commercially available 2-hydroxy-5-nonylacetophenone oxime, LIX 84 ®, available from Henkel Corporation. The product passed all the finished goods tests and copper extraction circuit tests of the commercially available product. The oxime of batch 4 had a somewhat higher copper max load, two separate dilutions at 10 v/v % in kerosene showing max loads of 4.97 and 4.97 g/l Cu compared to a specification of 4.80. In side-by-side circuits operating under the same extraction and stripping conditions on a sample of copper leach solution obtained from Twin Buttes, batch sample 4 gave a higher copper recovery than the commercial lot of oxime.

As a result of the foregoing, the preferred production scale of the present invention is a reaction carried out at a reaction temperature maintained at 90° C. with a reaction charge and wash charge in the order and quantities indicated in the following Table 5.

TABLE 5

| Material | Weight-kg |
|---|---|
| Reaction Charge: | |
| HNA | 3413 |
| Toluene | 683 |
| Sodium carbonate | 700 |
| Water | 190 |
| HAS | 950 |
| EHA | 90 |
| Wash Charge: | |
| Toluene | 1230 |
| Water (3 times) | 3000 |

EXAMPLE 7

In this example is described the preparation of 2-hydroxy-5-nonylbenzaldoxime, with and without phase transfer catalyst (PTC) assistance.

A mixture of 85.65 g of 2-hydroxy-5-nonylbenzaldehyde (NSA), [87% purity], (0.3 m); 27.54 g (0.17 m) of hydroxylammonium sulfate; 18.36 g (0.17 m) of sodium carbonate and 5.4 g (0.3 m) of water were combined and stirred with a mechanical stirrer at 67-70 deg. Samples of the organic phase were removed periodically and analyzed by HPLC. The results are summarized in the following tables:

TABLE 6

| | 250 rpm Agitation | |
|---|---|---|
| Time (min) | No PTC NSA % | With 1.57 g (3.6 m %) EHA NSA % |
| 30 | 12.04 | 3.7 |
| 45 | — | 1.64 |
| 75 | — | 0.56 |
| 80 | 9.89 | — |
| 90 | — | 0.21 |
| 100 | 7.52 | — |
| 125 | 4.65 | — |
| 170 | 0.48 | — |

TABLE 7

| | 350 rpm Agitation | |
|---|---|---|
| Time (min) | No PTC NSA % | With 1.57 g (3.6 m %) EHA NSA % |
| 30 | 14.67 | 2.4 |

TABLE 7-continued

| | 350 rpm Agitation | |
|---|---|---|
| Time (min) | No PTC NSA % | With 1.57 g (3.6 m %) EHA NSA % |
| 45 | — | 0.72 |
| 60 | — | 0.20 |
| 65 | 2.02 | — |
| 80 | 1.14 | — |
| 105 | 0.38 | — |

EXAMPLE 8

This example illustrates the oximation of a nonhydroxy ketone, 2-butanone.

A mixture of 21.6 g of 2-butanone (0.3 m); 25.8 g of HAS (0.16 m); 19.2 g of sodium carbonate (0.18 m) and 1.08 g of 2-EHA (2.5 m %) were stirred at room temperature with a paddle stirrer at approximately 350 rpm. About 2 ml of 5.4 ml water was added which caused the temperature to rise to 35° C. The remainder of the water was added incrementally over the next 15–20 min. The temperature rose to 40°, then dropped to room temperature. The reaction appeared to be complete in about 1 hr. The reaction mixture was diluted with toluene and water. The organic phase was washed twice with water after which the volatiles were removed at reduced pressure to leave 24.6 g (94% of theory) of residue, which GC/FTIR considered to be about 96 area % 2-butanone oxime.

EXAMPLE 9

This example illustrates the oximation of 2-hydroxy-5-nonylacetophenone (HNA) using a Rashig solution of hydroxylammonium sulfate (HAS). A synthetic Rashig solution of HAS was prepared by dissolving 33 g of HAS and 69 g of ammonium sulfate in 175 g of water and then adding 22.5 g sulfuric acid. The HNA was then oximated with the synthetic Rashig solution with and without phase transfer catalyst assistance.

A mixture of 64.5 g (0.2 m) of HNA [82% purity], and 164 g of synthetic Rashig solution (0.11 m HAS) were combined and stirred with a mechanical stirrer at about 350 rpm. The mixture was heated to 45° C. At that temperature 17 of 27 ml of 50% sodium hydroxide (41.5 g total) were added. The reaction temperature exothermed to 70°. The stirred mixture was heated to 90° and the remainder of the sodium hydroxide was added incrementally over 2 hr. Samples were removed periodically, diluted with toluene, washed with water, stripped of volatiles at reduced pressure and analyzed by GC/IR. The results are as follows:

| TIME | NO PTC | 5 m % VERSATIC ACID*, 42.3 g NaOH | 20 m % VERSATIC ACID**, 45.0 g NaOH |
|---|---|---|---|
| 2 hr | 81.8% HNA*** | 63.7% HNA*** | |
| 4 hr | 59.8 | 20.7 | |
| 4.5 hr | | | 8.9% HNA*** |
| 5.5 hr | | | 8.0 |
| 7 hr | | | 4.3 |
| 7.5 hr | 34.6 | 11.2 | |

*1.72 g
**6.88 g
***area % of volatiles

We claim:

1. In a method of preparing aliphatic or aromatic oximes with hydroxylamine the improvement which comprises conducting the reaction in the presence of about 0.001 to about 0.1 moles of an acid phase transfer catalyst; an alkali metal or alkaline earth metal hydroxide, carbonate or bicarbonate in at least a stoichiometric amount to the hydroxylamine; and water in an amount of about 0.1 to about 10 moles of water per mole of carbonyl.

2. A method as defined in claim 1, wherein said carbonyl compound is a ketone or aldehyde.

3. A method as defined in claim 1 wherein said acid phase transfer catalyst is an acid having from 4 to 20 carbon atoms.

4. A method as defined in claim 3, wherein said acid is 2-ethylhexanoic acid.

5. A method as defined in claim 1 wherein said acid phase transfer catalyst is 2-ethylhexanoic acid and said carbonate is sodium carbonate.

6. A method as defined in claim 5, wherein said 2-ethylhexanoic acid is present in an amount of about 0.04 moles of acid per mole of carbonyl and said carbonate is present in an amount of about 1.1 equivalents of carbonate to 1 equivalent of hydroxylamine.

7. A method as defined in claim 1, wherein said reaction is conducted in a non-alcoholic media containing water in an amount sufficient to wet the surfaces of the hydroxylamine and carbonate reactants.

8. A method as defined in claim 7, wherein the media further comprises a hydrocarbon solvent.

9. A method as defined in claim 8, wherein said hydrocarbon solvent is toluene.

10. A method as defined in claim 7, wherein said carbonyl compound is selected from the group consisting of 2-hydroxy-5-nonylacetophenone, 5-nonylsalicylaldehyde and 5-dodecylsalicylaldehyde, 2-hydroxy-5-dodecylacetophenone, butanone and 5,8-diethyl-7-hydroxydodecan-6-one.

11. A method as defined in claim 7 wherein the carbonyl compound is 2-hydroxy-5-nonylacetophenone, said acid phase transfer catalyst is 2-ethylhexanoic acid present in an amount of about 0.04 moles of acid per mole of carbonyl, the hydroxylamine is hydroxylammonium sulfate present in an amount of 1.1 equivalents to 1 equivalent carbonyl, said carbonate is sodium carbonate present in an amount of about 1.1 equivalents carbonate to 1 equivalent of hydroxylamine and the reaction is conducted at a temperature of greater than about 60° C. to about 90° C.

12. A process as defined in claim 11, wherein the reaction is conducted at a temperature of about 90° C.

13. A method as defined in claim 7, wherein the carbonyl compound is 5-nonylsalicylaldehyde or 5-dodecylsalicylaldehyde, said acid phase transfer catalyst is 2-ethylhexanoic acid present in an amount of about 0.04 moles of acid per mole of carbonyl, the hydroxylamine is hydroxylammonium sulfate present in an amount of 1.1 equivalents to 1 equivalent carbonyl, said carbonate is sodium carbonate present in an amount of about 1.1 equivalents carbonate to 1 equivalent of hydroxylamine and the reaction is conducted at a temperature of greater than about 35° C. to about 95° C.

14. A method of preparing a hydroxy oxime having the formula

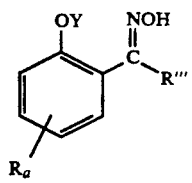

in which R is a saturated aliphatic group of 1–25 carbon atoms, an ethylenically unsaturated aliphatic group of 3–25 carbon atoms or —OR" where R" is a saturated or ethylenically unsaturated aliphatic group as defined; a is 0, 1, 2, 3, or 4; and R''' is a saturated aliphatic group of 1–25 carbon atoms or an ethylenically unsaturated aliphatic group of 3–25 carbon atoms, with the proviso that the total number of carbon atoms in $R_a$ and R''' is from 3 to 25 and Y is H or R''';

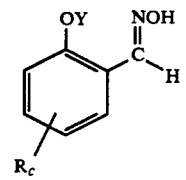

in which R and Y are as defined above with respect to Formula II, c has a value of 1, 2, 3 or 4, and the total number of carbon atoms in $R_c$ is from 3 to 25; or

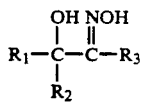

where $R_1$ and $R_3$ are alkyl groups of 1 to about 14 carbon atoms and $R_2$ is H or an alkyl group of 1 to about 14 carbon atoms, and the oxime being further characterized as having a total carbon atom content of 8 to 44, comprising in the presence of water in an ammount of about 0.1 to about 10 moles of water per mole of carbonyl (a) reacting a carbonyl compound corresponding to the hydroxy oxime defined above with hydroxylamine in the presence of
    (1) a catalytic amount of an acid phase transfer catalyst and
    (2) an alkali metal or alkaline earth metal hydroxide, carbonate or bicarbonate whereby the carbonyl group of the carbonyl compound is converted to the oxime group; and
(b) recovering the resulting oxime from the reaction mixture.

15. A method as defined in claim 14, wherein said phase transfer catalyst is an organic acid containing from about 4 to about 20 carbon atoms present in an amount of about 0.001 to about 0.1 moles of acid per mole of carbonyl, the hydroxylamine reactant is hydroxylammonium sulfate present in an amount of about 1.1 equivalents per equivalent of carbonyl, said carbonate is sodium carbonate present in an amount of about 1.1 equivalents carbonate to 1 equivalent of hydroxylamine, and the reaction is conducted at about 50° to about 90° C. in the presence of water in a sufficient amount to wet the surfaces of the hydroxylammonium sulfate and the carbonate.

16. A method defined in claim 15, wherein the carboxylic acid phase transfer catalyst is 2-ethylhexanoic acid present in an amount of about 0.04 moles of acid per equivalent of carbonyl, and the reaction is conducted with agitation at a temperature of about 90° C. in a non-alcoholic, hydrocarbon solvent reaction media for at least about 1 hour.

17. A method as defined in claim 16, wherein said hydrocarbon solvent is toluene.

18. A method as defined in claim 16, wherein said carbonyl component is selected from the group consisting of 2-hydroxy-5-nonylacetophenone, 2-hydroxy-5-dodecylacetophenone, 5-nonylsalicylaldehyde,5-dodecylsalicylaldehyde and 5,8-diethyl-7-hydroxydodecanone.

19. A method of preparing an alkyl salicylaldoxime in which the alkyl group contains from about 6 to about 11 carbon atoms comprising:
    (i) reacting an alkylsalicylaldehyde in which the alkyl groups contain from about 6 to about 11 carbon atoms with hydroxylamine in the presence of
        (x) an alkaline compound selected from the group consisting of an alkali metal or alkaline earth metal hydroxide, carbonate or bicarbonate, and
        (y) water in an amount only sufficient to wet the surface of the hydroxylamine and alkaline compound; and
    (ii) recovering the resulting oxime from the reaction mixture.

20. A method as defined in claim 19, wherein the hydroxylamine is present in an amount of at least 1 equivalent hydroxylamine to 1 equivalent of carbonyl, and the alkaline compound is present in an amount of at least 1 equivalent per equivalent of hydroxylamine.

21. A method as defined in claim 20, wherein the hydroxylamine is hydroxylammonium sulfate and the alkaline compound is sodium hydroxide or sodium carbonate.

22. A method as defined in claim 21, wherein the hydroxylammonium sulfate is present in an amount of about 1.1 equivalents to 1 equivalent carbonyl, and said alkaline compound is sodium carbonate, present in an amount of about 1.1 equivalents carbonate to 1 equivalent hydroxylamine.

23. A method as defined in claim 19, wherein the alkyl group in said salicylaldehyde contains from about 8 to about 10 carbon atoms.

24. A method as defined in claim 19, wherein said alkylsalicylaldehyde is nonylsalicylaldehyde.

25. A method as defined in claim 24, wherein the hydroxylamine is hydroxylammonium sulfate and said alkaline compound is sodium carbonate.

26. A method as defined in claim 25, wherein the reaction is conducted at a temperature of about 50° to about 90° C.

27. A method as defined in claim 26, wherein the hydroxylammonium sulfate is present in excess of 1 equivalent hydroxylamine per equivalent carbonyl and said carbonate is present in an amount in excess of 1 equivalent per equivalent of hydroxylamine.

28. A method as defined in claim 24, wherein the hydroxylamine is hydroxylammonium sulfate and said alkaline compound is sodium hydroxide.

29. A method as defined in claim 23, wherein the reaction is conducted at a temperature of about 50° to about 90° C.

30. A method as defined in claim 29, wherein the hydroxylamine is present in an amount in excess of 1 equivalent hydroxylamine per equivalent carbonyl and said hydroxide is present in an amount in excess of about 1 equivalent per equivalent of hydroxylamine.

31. A method as defined in claim 24, wherein the reaction is conducted in the presence of an inert, non-alcoholic hydrocarbon solvent.

32. A method as defined in claim 31, wherein said hydrocarbon solvent is toluene.

33. A method as defined in claim 32, wherein said alkyl salicylaldehyde is 5-nonylsalicylaldehyde, and the reaction is conducted at a temperature in the range of about 50° to about 90° C.

34. A method as defined in claim 33, wherein the hydroxylamine is hydroxylammonium sulfate employed in an amount in excess of 1 equivalent hydroxylamine per equivalent of carbonyl and said alkaline compound is sodium hydroxide or sodium carbonate and is present in an amount in excess of about 1 equivalent per equivalent of hydroxylamine.

* * * * *